United States Patent [19]

Reynolds

[11] 4,084,952
[45] Apr. 18, 1978

[54] USE OF ALKYL(AMINOCARBONYL)PHOSPHONATE SALTS IN RICE CULTURE FOR THE CONTROL OF PROBLEM HERBACEOUS PLANT GROWTH

[75] Inventor: James K. Reynolds, Kennett Square, Pa.

[73] Assignee: E. I. Du Pont de Nemours and Company, Wilmington, Del.

[21] Appl. No.: 699,934

[22] Filed: Jun. 25, 1976

[51] Int. Cl.² .................................................. A01N 9/36
[52] U.S. Cl. ................................................. 71/86; 71/76; 71/DIG. 1
[58] Field of Search ................................................. 71/86

[56] References Cited

U.S. PATENT DOCUMENTS

| 3,005,010 | 10/1961 | Grisley, Jr. | 260/941 |
|---|---|---|---|
| 3,619,166 | 11/1971 | Quebedeaux, Jr. | 71/86 |
| 3,849,102 | 11/1974 | Bucha et al. | 71/86 |
| 3,952,074 | 4/1976 | Langsdorf | 71/86 |
| 4,017,296 | 4/1977 | Hernandez | 71/86 |
| 4,017,297 | 4/1977 | Hernandez | 71/86 |
| 4,018,854 | 4/1977 | McIntosh | 71/86 |

OTHER PUBLICATIONS

Zandstra et al., "Response of purple nutsedge, etc.;" (1974) CA81, No. 59195t, (1974).
Suwunnamek et al., "Control of *C. rotundus* with etc.;" (1975) CA83, No. 108660e, (1975).
Schwarz, "Herbicidal O-ethyl S,S-diphenyl, etc.;" (1974) CA82, No. 12273x, (1975).
Palmer et al., "Rice weed control in the western, etc.;" (1974) CA81, No. 86669g, (1974).

*Primary Examiner*—Glennon H. Hollrah

[57] ABSTRACT

Alkyl(aminocarbonyl)phosphonate salts are added to rice cultures in order to control problem herbaceous plant growth.

3 Claims, No Drawings

USE OF ALKYL(AMINOCARBONYL)PHOSPHONATE SALTS IN RICE CULTURE FOR THE CONTROL OF PROBLEM HERBACEOUS PLANT GROWTH

BACKGROUND OF THE INVENTION

A broad range of alkyl(aminocarbonyl)phosphonate salts is disclosed in U.S. Pat. No. 3,846,512. These compounds are extremely useful as plant growth regulants.

The presence of undesired vegetation in rice is an especially important problem for the world at this time. Faced with the current world situation, wherein food shortages are acute in many different areas, it is most important not to lose a portion of a valuable crop such as rice because of the presence of this undesired vegetation. In particular, two kinds of herbaceous weeds, arrowhead, *Sagittaria* sp. and nutsedge, *Cyperus serotinus* or *rotundus* are especially troublesome for rice crops. In the past, these herbaceous weeds have been extremely difficult to control. Thus, a need exists for a particularly effective compound which will control the growth of these weeds and prevent them from damaging a significant part of the rice crop.

SUMMARY OF THE INVENTION

According to this invention, it has unexpectedly been discovered that a compound of Formula I may be utilized for the post-harvest control of arrowhead, *Sagittaria sp.* and nutsedge *Cyperus serotinus* or *rotundus*.

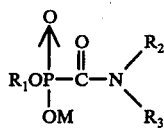

Formula I wherein $R_1$ is alkyl of 1 through 8 carbon atoms, chloroalkyl of 1 through 8 carbon atoms containing up to 3 chlorine atoms, bromoalkyl of 1 through 8 carbon atoms containing up to 3 bromine atoms, alkoxy alkyl of from 3 through 10 carbon atoms, total, alkenyl of 2 through 8 carbon atoms, alkynyl of 3 through 4 carbon atoms, phenyl or benzyl;

$R_2$ and $R_3$ can be the same or different and each can be hydrogen, alkyl of 1 through 4 carbon atoms, hydroxy alkyl of 2 through 4 carbon atoms, alkenyl of 3 through 4 carbon atoms, alkynyl of 3 through 4 carbon atoms; $R_2$ and $R_3$ can be taken together to form a ring wherein $R_2$ and $R_3$ taken together are $-(CH_2)_2-O-(CH_2O_2-$ or $-(CH_2)_n-$ where $n$ is 4, 5 or 6 or one of $R_2$ and $R_3$ can be

where $R_4$ is hydrogen or alkyl of 1 through 4 carbon atoms and $R_5$ is hydrogen or alkyl of 1 through 4 carbon atoms, and M is hydrogen, sodium, lithium, potassium, calcium, magnesium, zinc, manganese, barium or

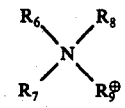

where $R_6$, $R_7$ and $R_8$ can be the same or different and each can be hydrogen, alkyl of 1 through 4 carbon atoms or hydroxy alkyl of 2 through 4 carbon atoms; and $R_9$ is hydrogen, alkyl of 1 through 12 carbon atoms,

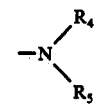

where $R_4$ is hydrogen or alkyl of 1 through 4 carbon atoms and $R_5$ is hydrogen or alkyl of 1 through 4 carbon atoms or benzyl.

Preferred for their high biological activity are those compounds of formula I where, independently:
(a) $R_1$ is alkyl of 1 through 4 carbon atoms or alkenyl of 3 through 4 carbon atoms,
(b) $R_2$ and $R_3$ are both equal to hydrogen,
(c) M is ammonium or an alkali metal such as sodium, lithium or potassium.

More preferred for their higher activity are those compounds of formula I where $R_1$ is alkyl of 1 through 4 carbon atoms, $R_2$ and $R_3$ are both hydrogen and M is ammonium or an alkali metal such as sodium, lithium or potassium.

Specifically preferred for their outstanding herbicidal activity are:
(a) Ammonium ethyl (aminocarbonyl) phosphonate m.p. 173°–176° C
(b) Ammonium methyl (aminocarbonyl) phosphonate m.p. 148°–152° C.

PREPARATION OF THE COMPOUND

The compounds of the instant invention may be prepared according to the process disclosed in U.S. Pat. 3,846,512, the disclosure of which is herein incorporated by reference.

Basically, the process involves the following equation:

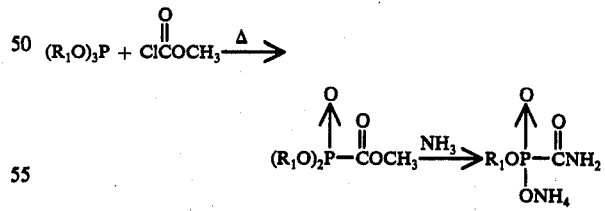

FORMULATION OF THE COMPOUNDS

The growth controlling compositions of the present invention can be prepared by admixing at least one of the compounds of this invention with pest control adjuvants or modifiers to provide compositions in the form of dusts, water-soluble powders, solutions, granules or pellets.

Compositions of the invention may contain as a conditioning agent, one or more surface-active agents, sometimes called surfactants, in amounts sufficient to render a given composition containing the compound of this invention readily soluble in water or capable of wetting foliage efficiently.

The surface-active agent used in this invention can be a wetting, dispersing or an emulsifying agent which will assist dispersion and solution of the active compound. The surface-active agent or surfactant can include such anionic, cationic and non-ionic agents as have heretofore been generally employed in plant control compositions of similar type. Suitable surface-active agents are set forth, for example, in "Detergents and Emulsifiers", 1975 Annual by John W. McCutcheon, Inc.

In general, less than 10% by weight of the surface-active agent will be used in compositions of this invention and ordinarily the amount of surface-active agents will range from 1–5% but may even be less than 1% by weight.

Additional surface-active agents can be added to the formulations to increase the ratio of surfactant:active ingredient up to as high as 5:1 by weight. Such compositions may have a greater effectiveness than can be expected from a consideration of the activity of the components used separately. When used at higher rates, it is preferred that the surfactant be present in the range of one-fifth to five parts surfactant for each one part of active agent.

WATER-SOLUBLE POWDERS

Water-soluble powders are compositions containing the water-soluble active material, an inert solid extender which may or may not be water-soluble, and optionally one or more surfactants to provide rapid wetting and solution. A buffer, which may also function as an extender, can be present to improve formulation stability and control the pH of the final spray solution.

The classes of extenders suitable for the water-soluble powder formulations of this invention are the natural clays, diatomaceous earth, synthetic mineral fillers derived from silica and silicate, starch, sugar, and inorganic salts. Most preferred fillers for this invention are kaolinites, attapulgite clay, montmorillonite clays, synthetic silicas, synthetic magnesium silicate, calcium sulfate dihydrate, and disodium hydrogen phosphate.

Suitable surfactants for use in such compositions are those listed by J. W. McCutcheon in "Detergents and Emulsifers", 1975 Annual. Among the more preferred surfactants are the non-ionic and anionic types, and those most suitable for the preparation of the dry, soluble products of this invention are solid forms of compounds known to the art as wetters and dispersants. Occasionally a liquid, non-ionic compound classified primarily as an emulsifier may serve as both wetter and dispersant.

Most preferred wetting agents are alkylbenzene- and alkylnaphthalene-sulfonates, sulfated fatty alcohols, amines or acid amides, long-chain acid esters of sodium isethionate, esters of sodium sulfosuccinate, sulfated or sulfonated fatty acid esters, petroleum sulfonates, sulfonated vegetable oils and ditertiary acetylenic glycols. Preferred dispersants are methylcellulose, polyvinyl alcohol lignin sulfonates, polymeric alkylnaphthalenesulfonates, sodium naphthalenesulfonate, polymethylene bisnaphthalenesulfonate, and sodium N-methyl-N-(long chain acid)taurates.

Wetting and dispersing agents in these preferred water-soluble compositions of this invention are usually present at concentrations of from about 0.5 weight percent to 5 weight percent. The inert extender then completes the formulation. Where needed, 0.1 weight percent to 1.0 weight percent of the extender may be replaced by a corrosion inhibitor or an anti-foaming agent or both.

Thus, water-soluble formulations of the invention will contain from about 25 to 95 weight percent active material, from 0.5 to 2.0 weight percent wetting agent, from 0.25 to 0.5 weight percent dispersant, and from 4.25 to 74.25 weight percent inert extender, as these terms are described above.

When the water-soluble powder contains a corrosion inhibitor or an anti-foaming agent or both, the corrosion inhibitor will not exceed about 1 percent of the composition, and the anti-foaming agent will not exceed about 0.5 percent by weight of the composition, both replacing equivalent amounts of the inert extender.

SOLUTION CONCENTRATES

The aqueous solution concentrates are prepared by mixing a water-soluble active compound of this invention with water. A portion of the water may be replaced with methanol, ethanol, isopropanol, ethylene glycol, cellosolve or methyl cellosolve. Surfactants and buffering agents can optionally be present.

These aqueous solution concentrates will contain from 15 to 60 percent active ingredient and from 40 to 85 percent water or mixture of water and hydroxylated organic solvent. Surfactants, corrosion inhibitors, buffering and antifoam agents may also be included in which case they may replace up to 10 percent of the solvent system.

DUSTS

Dusts are dense powder compositions which are intended for application in dry form, in accordance with the preferred compositions and methods of the invention. Dusts are characterized by their free-flowing and rapid settling properties so that they are not readily windborne to areas where their presence is not desired. They contain primarily an active material and a dense, free-flowing, solid extender.

Their performance is sometimes aided by the inclusion of a wetting agent, and convenience in manufacture frequently demands the inclusion of an inert, adsorptive grinding aid. For the dust compositions of this invention, the inert extender may be either of vegetable or mineral origin, the wetting agent is preferably anionic or non-ionic and suitable adsorptive grinding aids are of mineral origin.

Suitable classes of inert solid extenders for use in the dust compositions are those organic or inorganic powders which possess high bulk density and are very free-flowing. They are also characterized by possessing relatively low surface areas and are poor in liquid adsorption. Suitable classes of grinding aids are natural clays, diatomaceous earths, and synthetic mineral fillers derived from silica or silicate. Among ionic and non-ionic wetting agents, the most suitable are the members of the group known to the art as wetting agents and emulsifiers. Although solid agents are preferred because of ease of incorporation some liquid non-ionic agents are also suitable in the dust formulations.

Preferred inert solid extenders for the dusts of this invention are micaceous talcs, pyrophyllite, dense kaolin clays, tobacco dust and ground calcium phosphate rock.

Preferred grinding aids are attapulgite clay, diatomaceous silica, synthetic fine silica and synthetic calcium and magnesium silicates. Preferred wetting agents are those previously described under water-soluble powder formulations.

The inert solid extenders in the dusts of this invention are usually present in concentration of from about 30 to 90 weight percent of the total composition. The grinding aid will usually constitute 5 to 50 weight percent of the composition, and the wetting agent will constitute from 0 to 1.0 weight percent of the composition. Dust compositions can also contain other surfactants such as dispersing agents in concentrations of up to about 0.5 weight percent.

The water-soluble powders described above can also be used in the preparation of dusts. While such water-soluble powders could be used directly in dust form, it is more advantageous to dilute them by blending with the dense dust diluent. In this manner, dispersing agents, corrosion inhibitors, and anti-foam agents may also be found as components of a dust.

Thus, the dust compositions of this invention will comprise about 5 to 20 weight percent active material, 5 to 50 weight percent adsorptive filler, 0 to 1.0 weight percent wetting agent, and about 30 to 90 weight percent dense, free-flowing dust diluent, as these terms are used herein. Such dust formulations can contain, in addition, minor amounts of dispersants, corrosion inhibitors, and anti-foam agents, derived from the water-soluble powders used to make the dusts.

GRANULES AND PELLETS

Under some circumstances it may be advantageous to apply the compounds of this invention in the form of granules or pellets. Suitable carriers are natural clays, some pyrophyllites and vermiculites. Wetting agents of the type listed by J. W. McCutcheon in "Detergents and Emulsifiers", 1975 Annual can also be present to aid leaching of the active component.

One method of preparation suitable for both granules and pellets involves blending the active ingredient with clays, water-soluble salts, surfactants and a small amount of water. After pelleting and/or granulating, the formulation is dried prior to use. A second method suitable for the preparation of granules formulation involves spraying a solution of the active material on porous, adsorptive, preformed clay or vermiculite granules. Surfactants listed by McCutcheon can also be included in the spray solution. After drying, the granules are ready for application.

The preferred granules or pellets will contain about 5 to 30 weight percent of active material, about 0 to 5 weight percent wetting agent and about 65 to 95 weight percent inert mineral carrier.

UTILITY

The carbamoylphosphonic salts of this invention may be used to control certain persistent weeds in rice paddies after the harvest of one rice crop and prior to the planting of the next. These weeds, such as arrowhead and nutsedge are not controlled by currently used selective rice herbicides. When sprayed on the foliage of the weeds while they are growing, but after rice harvest, the phosphonates of this invention cause retardation and prevent bud-break on the vegetative propagules (stolons or tubers) of these species. This effectively controls the plant the following season. These chemicals have little or no effect on plants through the soil and cause no reaction in the following crop.

The compounds may be applied at rates of 1 to 20 kg/ha in sufficient carrier to distribute them uniformly over the leaves of the weeds. Treatment must be applied while the weeds are green and growing to insure that it will be translocated to the stolons or tubers. However, it must not be applied before the crop is harvested.

EXAMPLE 1

Arrowhead, *Sagittaria* sp., was treated with ammonium ethyl(aminocarbonyl)phosphonate after water had been drained from experimental rice pots at the rate of approximately 2-½ kg/ha. This treatment caused marked growth retardation and prevented regrowth in the pots.

EXAMPLE 2

Nutsedge, *Cyperus serotina*, growing in experimental pots was treated with rates of ammonium ethyl(aminocarbonyl)phosphonate at rates of 2-½, 5 and 10 kg/ha. Two and one-half months later the tubers were dug from treated and control pots and their germination determined. The results are shown below.

| Treatment | Rate, kg/ha | Tubers Number | Weight g. | Germination |
|---|---|---|---|---|
| Phosphonate | 10 | 15 | 2 | none |
|  | 5 | 12 | 2 | none |
|  | 2½ | 27 | 4 | none |
| Control | — | 262 | 57 | good |

EXAMPLE 3

Nutsedge, *Cyperus rotundus*, was treated with a foliar spray of ammonium ethyl(aminocarbonyl)phosphonate or ammonium methyl(aminocarbonyl)phosphonate (B) in early September. The data below were taken the last of April the next season. The results show that the treatment effectively reduced the stand of nutsedge the next spring.

| Treatment | Rate, kg/ha | Nutsedge at Application on 9/9 | Cover Nutsedge 4/4 |
|---|---|---|---|
| A | 4 | 100 | 95 |
|  | 8 | 100 | 80 |
|  | 12 | 100 | 50 |
| B | 4 | 100 | 90 |
|  | 8 | 100 | 35 |
|  | 12 | 100 | 15 |

What is claimed is:

1. A method for the control of arrowhead or nutsedge weeds in rice fields which comprises applying to the foliage of the weeds while they are growing, but after rice harvest, an effective amount of a compound of the formula $$R_1OP(=O)(OM)-C(=O)-N(H)(H)$$

wherein
$R_1$ is alkyl of 1 through 4 carbon atoms, or alkenyl of 3–4 carbon atoms;
M is hydrogen, ammonium or an alkali metal.

2. The method of claim 1 wherein the compound is ammonium ethyl(aminocarbonyl)phosphonate.

3. The method of claim 1 wherein the compound is ammonium methyl(aminocarbonyl)phosphonate.

* * * * *